United States Patent [19]

Amundsen et al.

[11] Patent Number: 5,437,275

[45] Date of Patent: Aug. 1, 1995

[54] PULSE OXIMETRY SENSOR

[75] Inventors: Neil T. Amundsen, Milwaukee; Glenn T. Walters, Port Washington, both of Wis.

[73] Assignee: Biochem International Inc., Waukesha, Wis.

[21] Appl. No.: 190,817

[22] Filed: Feb. 2, 1994

[51] Int. Cl.⁶ .............................................. A61B 5/00
[52] U.S. Cl. ................................................... 128/633
[58] Field of Search .............................. 128/633–634, 128/664–667; 356/39–41

[56] References Cited

U.S. PATENT DOCUMENTS

| | | | |
|---|---|---|---|
| 5,035,243 | 7/1991 | Muz | 128/633 |
| 5,246,003 | 9/1993 | DeLonzor | 128/633 |
| 5,311,865 | 5/1994 | Mayeux | 128/633 |
| 5,339,810 | 8/1994 | Ivers et al. | 128/633 |

Primary Examiner—Angela D. Sykes
Attorney, Agent, or Firm—Quarles & Brady

[57] ABSTRACT

A pulse oximetry sensor comprises a photoemitter; a photodetector; and, a generally tubular housing having an inner wall, an outer wall and a lumen for receiving a body part of a patient. The housing has a pair of opposed pockets for removably receiving the photoemitter and the photodetector, respectively. Each of the pockets has a bottom window through which light can pass and an open top. The housing also has side passages between the inner wall and the outer wall of the housing through which the photoemitter and the photodetector can be introduced into and removed from their respective pockets.

17 Claims, 3 Drawing Sheets

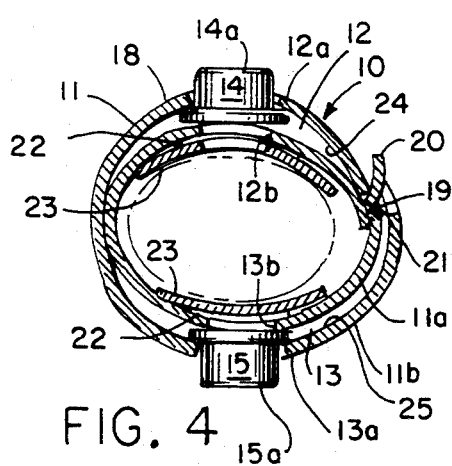
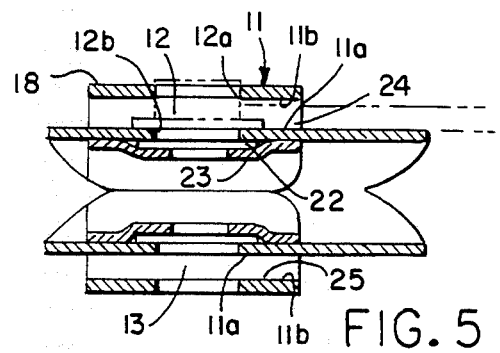
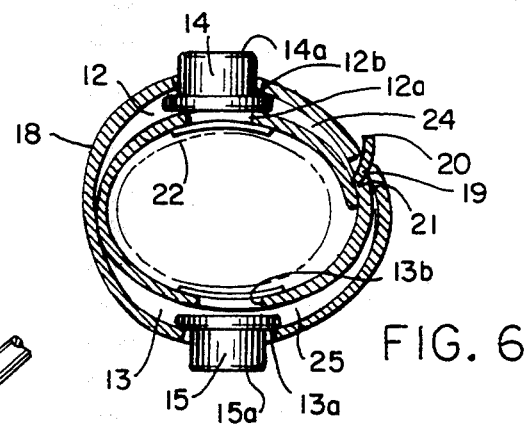
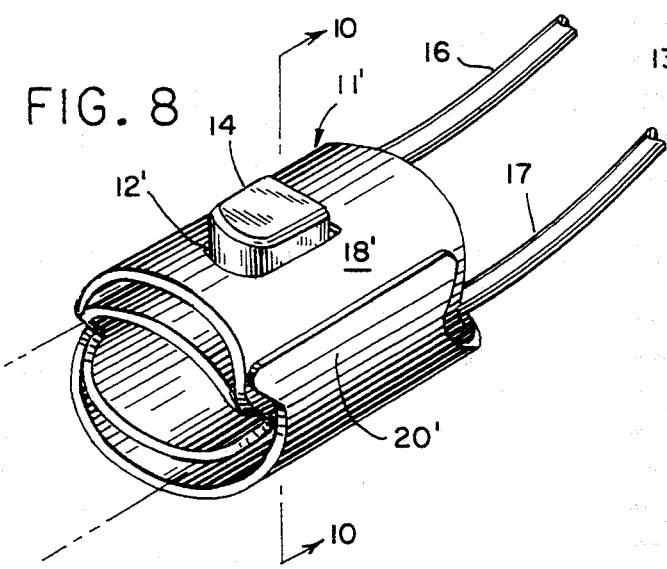
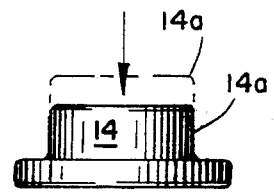
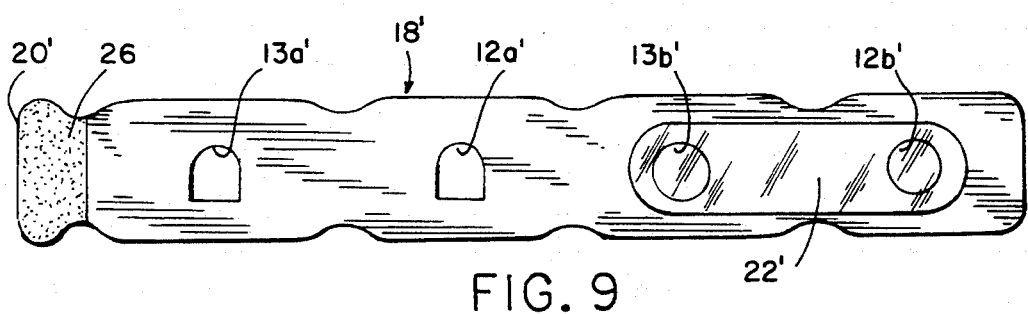

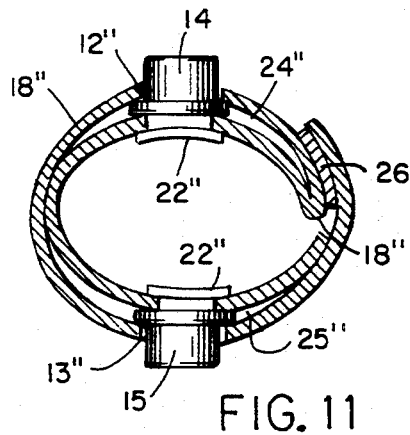
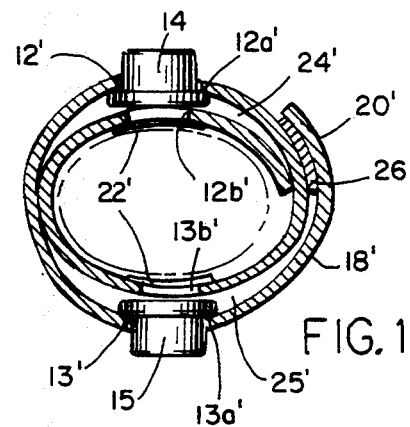
FIG. 11  FIG. 10
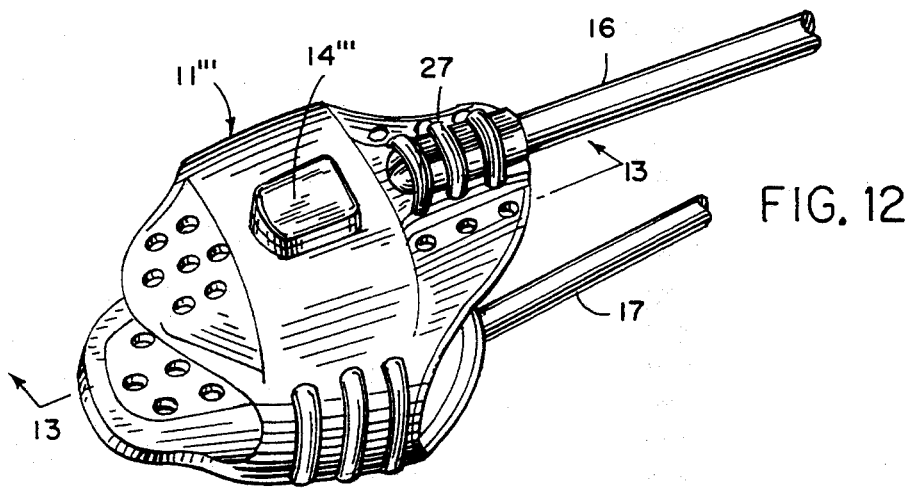
FIG. 12
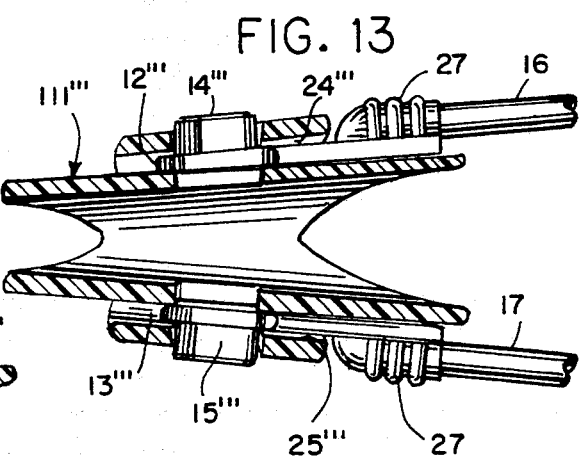
FIG. 13
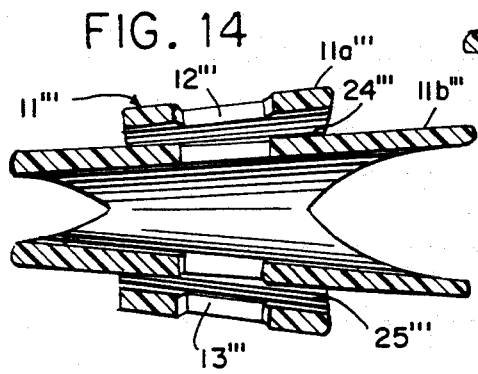
FIG. 14

PULSE OXIMETRY SENSOR

FIELD OF THE INVENTION

The present invention generally relates to medical sensors for detecting physiological functions. More particularly, it relates to an optical sensor for a pulse oximetry system.

BACKGROUND OF THE INVENTION

Pulse oximetry is a non-invasive technique which is useful for measuring certain vascular conditions. In pulse oximetry, light is passed through a portion of a patient's body, which contains arterial blood flow. An optical sensor detects the light which has passed through the body, and the variations in the detected light at various wavelengths are then used to determine the arterial oxygen saturation and/or pulse rates. Oxygen saturation may be calculated using the absorption equation known as Beer's Law.

The accurate measurement of oxygen saturation is dependent upon several factors which affect the supply of blood in the body part that is being used for the measurement. For example, blood flow can be affected by vasoconstriction. One cause of vasoconstriction can be the pressure exerted by the sensor on the finger or other body part of the patient. Many currently available pulse oximetry sensors have a hard shell which is maintained on a finger by the action of a spring. Since excessive pressure on the finger can dampen or eliminate the pulsations in the finger's blood supply, these springs are intentionally made very soft. The result is that such spring-held sensors are not completely satisfactory because they may fall off the finger.

A sensor that does not employ a spring is described in the Thomas et al. U.S. Pat. No. 5,170,786. The pressure exerted by that sensor is determined by the tightness with which the sensor is wrapped about a finger. However, that sensor is not readily preassembled and it could be relatively expensive to make.

It would be desirable to have a sensor which can be preassembled, which does not employ a spring and which is inexpensive enough to be disposed of after a single use.

BRIEF SUMMARY OF THE INVENTION

It is an object of the present invention to disclose a novel, inexpensive pulse oximetry sensor with a novel housing which can be readily preassembled and which can be disposed of after a single use.

It is further an object to disclose a sensor housing which isolates the electrical components of the sensor from direct contact with the patient and which permits the subsequent reuse of the electrical components of the sensor.

The sensor of the present invention comprises a photoemitter; a photodetector; and a novel sensor housing. The novel tubular sensor housing has an inner wall, an outer wall and a lumen to receive a body part. It also has a pair of opposed pockets for removably receiving the photoemitter and the photodetector, respectively. Each of the pockets has a bottom window, which can be covered by a film which is impervious to microorganisms, viruses, or the like, and an open top. The housing also has side entrances between the inner and outer wall through which the photoemitter and the photodetector can be inserted into or removed from the pockets.

In one preferred embodiment of the invention, the sensor housing is made of a wrap of a disposable material, such as paper, which can be either pre-assembled into the desired shape before use, or custom formed into the desired shape on the patient at the time of use. The photoemitter and photodetector can be either placed in their respective pockets at the factory or by an operator at the time of use.

In still another embodiment, the housing is molded of plastic.

It will be readily apparent to those skilled in the art from the drawings and description which follows that the above objectives and additional advantages can be achieved by the practice of the present invention.

BRIEF DESCRIPTION OF THE DRAWINGS

In the drawings:

FIG. 4 is a view taken along line 4—4 in FIG. 1;

FIG. 5 is a view taken along line 5—5 in FIG. 2;

FIG. 6 is a view like FIG. 4 of a second embodiment of the sensor housing of the present invention;

FIG. 7 is an enlarged view, partly in section, of a photoemitter with its top depressed shown in solid lines and its top not depressed shown in broken lines;

FIG. 8 is a perspective view of another embodiment of the sensor of the present invention;

FIG. 9 is a top view of the wrap from which the sensor housing of the sensor of FIG. 8 is prepared;

FIG. 10 is a view taken along line 10—10 in FIG. 8;

FIG. 11 is a view like FIG. 10 of a sensor housing made of another wrap;

FIG. 12 is a perspective view of still another embodiment of the sensor of the present invention;

FIG. 13 is a view taken along line 13—13 in FIG. 12; and

FIG. 14 is a view like FIG. 13 of the sensor housing of FIG. 12 without the photoemitter and photodetector.

DESCRIPTION OF THE PREFERRED EMBODIMENT

Figure 1:
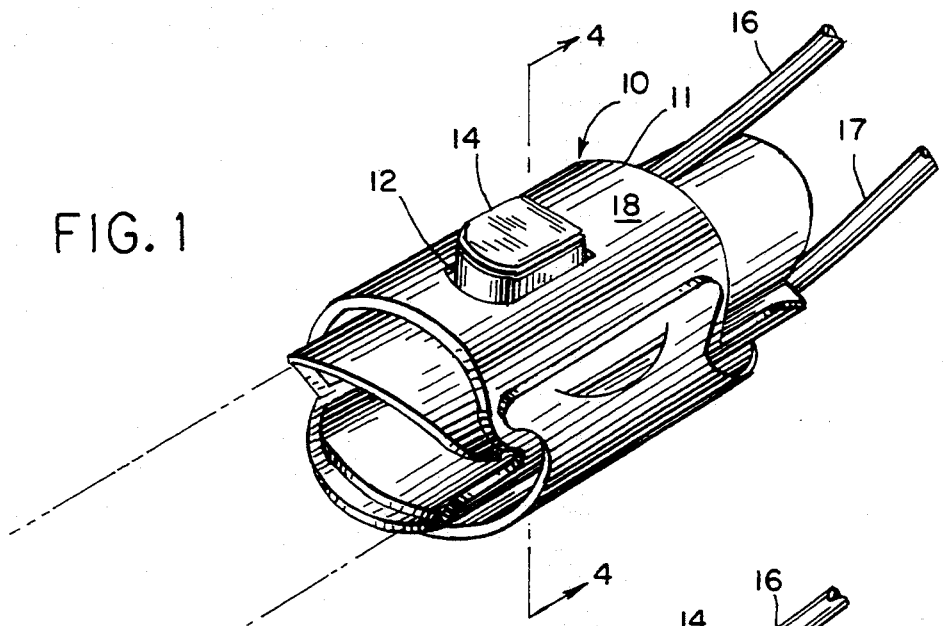
FIG. 1 is a perspective view of one embodiment of the sensor of the invention.

In the preferred embodiment shown in FIGS. 1 to 5, the oximetry sensor 10 of the present invention comprises a tubular housing 11, having a pair of directly opposed pockets 12 and 13 (seen best in FIGS. 4 and 5) which contain a photoemitter 14 and a photodetector 15, respectively.

A red light emitting diode (LED) and an infrared light emitting diode (LED) (neither shown) are adjacently mounted in the photoemitter 14 to alternately radiate red and infrared energy through the finger of the patient.

In oximetry, the transmission of light in the red range of the spectrum, i.e., at a wave length of approximately 660 nanometers through blood is substantially affected by the amount of oxygenated hemoglobin present in the blood. The transmission of light in the infrared range of the spectrum, i.e., at a wave length of approximately 940 nanometers through blood is substantially unaffected by the amount of oxygenated hemoglobin present in the blood. Oximeters use this principal to alternately illuminate the blood through the skin tissue with light of the foregoing respective wave lengths. Hence, in accordance with the present invention, the one LED emits light in the red range at 660 nm and the second LED emits light in the infrared range at approximately 940 nm.

The photodetector 15 is sensitive to red light and infrared light and receives and senses alternately radiated red and infrared energy from the photoemitter 14. The photodetector 15 transmits signals to an oximeter monitor (not shown) in response to received red and infrared light.

The photoemitter 14 and photodetector 15 are operatively connected to the oximeter monitor (not shown) by the cables 16 and 17, respectively.

Figure 2:
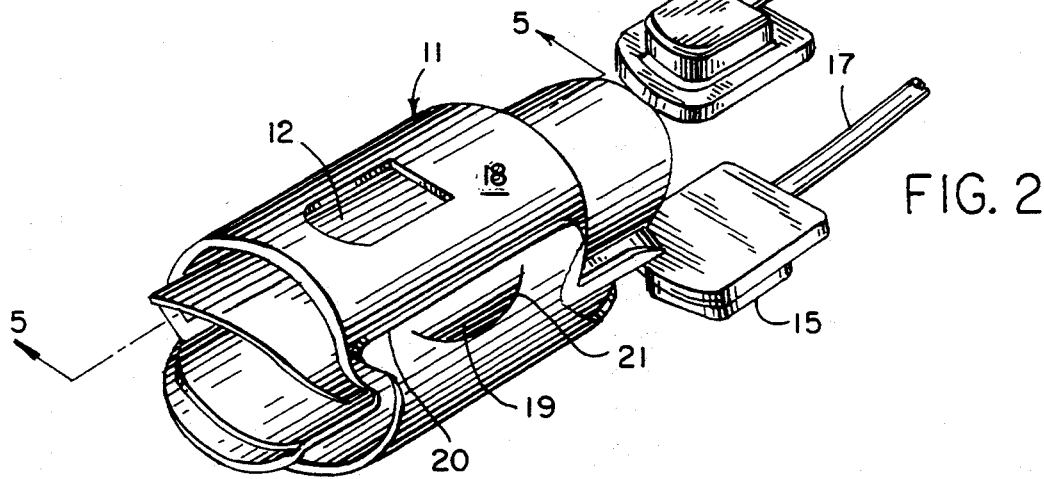
FIG. 2 is an exploded view of the sensor of FIG. 1.
Figure 3:
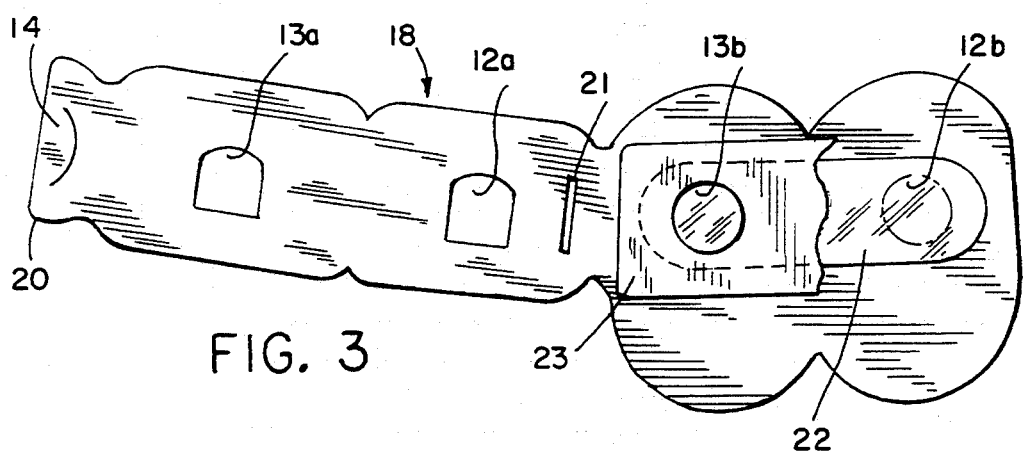
FIG. 3 is a top view, partly in section, of the wrap from which the sensor housing of the sensor of FIG. 1 is formed.

In FIG. 3 a wrap 18 is shown which can be used to form the housing 11. The wrap 18 can be used to either preassemble the housing 11 in a factory or to form the housing 11 about a patient's body part, such as an adult's finger or an infant's toe, at the time of use. When the wrap 18 is assembled into a housing 11, a tab 19 at one end 20 of the wrap 18 is tucked into a slot 21 of the wrap 11, as seen in FIGS. 1, 2 and 4. When the housing 11 is assembled the pockets 12 and 13, which have open tops which are formed by the apertures 12a and 13a and bottom windows which are formed by circular apertures 12b and 13b, are opposed.

In the embodiment of the sensor housing 11 shown in FIGS. 1 to 5 the circular apertures 12b and 13b are covered by a transparent film 22 and there is a thin layer of cushioning material 23, such as foam, between the film 22 and the patient's body.

Still referring to FIGS. 1 to 5, it can be seen in FIG. 5 that there are side entrance passages 24, 25 between the inner wall 11a and outer wall 11b of the housing 11 through which the photoemitter 14 and photodetector 15 can be introduced into or removed from the pockets 12 and 13, respectively.

The movement of the photoemitter 14 and photodetector 15 through passages 24, 25 can be facilitated when the wrap 18 is of a non-elastomeric material, such as paper, by making the tops 14a and 15a of the housings of the photoemitter 14 and photoreceptor 15 deformable so that they can be squeezed to make them shorter (see FIG. 7) before introducing them into the passages 24 or 25. Once in place the tops 14a and 15a can be allowed to expand to protrude out the apertures 12a and 13a as seen in FIG. 1. Thus, the photoemitter 14 and photoreceptor 15 can be securely retained in operative position in the sensor housing 11.

When the oximetry procedure is over the tops 14a and 15a can once again be deformed to shorten their height and to facilitate their entrance into the passages 24, 25 and their subsequent removal from the pockets 12 and 13. If the wrap 18 is of an elastomeric material, such as a rubber, it is not necessary that the tops 14a and 15a be deformable.

When the photoemitter 14 and detector 15 are removed, the housing 11 can be discarded. The photoemitter 14 and photodetector 15, because they have not been in direct contact with the patient's skin because of the transparent film 22, can then be reused, if desired.

The embodiment of FIG. 6 is substantially identical to that of FIGS. 1 to 5 except that there is no cushioning material 23.

In the embodiment of the invention seen in FIGS. 8 to 10, the wrap 18' (seen best in FIG. 9) is intended to form a housing 11' for an infant's foot. One end 20' of the wrap 18' is coated with a suitable pressure sensitive adhesive 26 (best seen in FIG. 9) which is covered with a release liner (not shown). When the wrap 18' is assembled into the sensor housing 11' the various elements 12', 13', 12a', 13a', 12b', 13b', 22' and 24' are positioned and operate essentially as described for the embodiment of FIGS. 1 to 5. FIG. 11 shows another housing 11'' made from a wrap 18'' of a different configuration which permits the wrap to be folded back along itself to form the pocket 12''.

In FIGS. 12 to 14 a housing 11''' molded of a plastic, such as polyvinyl chloride, is shown which includes pockets 12''' and 13''' into which a photoemitter and photodetector can be inserted. As seen therein, the housing 11''' includes passages 24''', 25''' via which the photoemitter 14''' and photodetector 15''' can be inserted in their respective pockets. Although the photoemitter 14''' and photodetector 15''' have gripping means 27 and they are differently shaped, they are inserted and removed in substantially the same manner as described for the photoemitter 14 and photodetector 15 in connection with the embodiment of FIGS. 1 to 5.

It will be readily apparent to those skilled in the art that a number of modifications or changes can be made without departing from the spirit and scope of the present invention. Therefore, it is intended that the invention only be limited by the claims.

We claim:

1. A pulse oximetry sensor comprising a photoemitter; a photodetector; and, a generally tubular housing having an inner wall, an outer wall and a lumen for receiving a body part of a patient; said housing having a pair of opposed pockets formed between the inner wall and the outer wall for removably receiving the photoemitter and the photodetector, respectively, said pockets each having a window in the inner wall through which light can pass and an aperture in the outer wall which aperture receives a portion of a respective one of the photoemitter and the photodetector; said housing also having side passages between the inner wall and the outer wall with each passage having an opening in the housing through which the photoemitter and the photodetector can be introduced into and removed from their respective pockets.

2. A sensor of claim 1 in which the window of the housing is covered with a light transparent film.

3. A sensor of claim 1 in which the housing is formed from a wrap of disposable material.

4. A sensor of claim 1 in which the housing is molded of plastic.

5. A sensor of claim 1 in which the photoemitter and photodetector have deformable tops which are received in the aperture of a respective pocket.

6. A housing for a pulse oximetry sensor, said housing being a tubular body having an inner wall, an outer wall and a lumen for receiving a body part of a patient, said housing having a pair of opposed pockets for removably receiving a photoemitter and a photodetector, respectively, each of said pockets having a window in the inner wall through which light can pass and an aperture in the outer wall which aperture receives a portion of a respective one of the photoemitter and the photodetector, said housing also having passages between the inner wall and the outer wall with each passage having an opening in the housing through which a photoemitter and a photodetector can be introduced into and removed from the pockets.

7. A housing of claim 6 in which each of the windows is covered by a light transparent film.

8. A housing of claim 7 in which the housing is formed of a disposable material.

9. A housing of claim 7 in which the inner and outer walls are formed of a wrap of disposable material.

10. A housing of claim 9 wherein the disposable material is paper.

11. A housing of claim 6 in which the housing is molded of plastic.

12. A generally tubular housing for a pulse oximeter sensor, said housing having an inner wall with a pair of opposed windows and an outer wall with a pair of apertures aligned with said windows so that a pair of opposed pockets for receiving a photoemitter and a photodetector are formed with each pocket having a window at the bottom and an aperture at the top, said inner and outer walls being spaced apart to form side passages with an opening in the housing through which either the photoemitter or the photodetector can be introduced into one or both of said pockets.

13. A housing of claim 12 in which the inner wall includes a layer of cushioning material.

14. A housing of claim 12 in which the window is covered by a transparent film.

15. A housing for a pulse oximeter sensor, said housing formed by a strip of material coiled in a spiral to form an inner wall, an outer wall and a lumen, with a pair of opposed pockets being formed between the inner and outer walls for receiving a photoemitter and a photodetector, respectively, each pocket having a window that extends through the inner wall; the inner and outer walls are spaced apart to form passages through which one of the photoemitter and the photodetector can be introduced into each of the pockets.

16. A housing of claim 15 wherein each pocket has an aperture aligned with the window for receiving a portion of one of the photoemitter and the photodetector.

17. A sensor of claim 16 further comprising a transparent film applied to a surface of the strip of material and extending across each window.

* * * * *